(12) United States Patent
Zia et al.

(10) Patent No.: US 8,092,413 B2
(45) Date of Patent: *Jan. 10, 2012

(54) MULTI-PURPOSE TUBING APPARATUS

(76) Inventors: Majid Zia, White Bear Township, MN (US); Anthony J. Angelo, Forest Lake, MN (US); Craig M. Wilson, Minneapolis, MN (US)

( * ) Notice: Subject to any disclaimer, the term of this patent is extended or adjusted under 35 U.S.C. 154(b) by 144 days.

This patent is subject to a terminal disclaimer.

(21) Appl. No.: 11/931,525

(22) Filed: Oct. 31, 2007

(65) Prior Publication Data

US 2008/0058714 A1    Mar. 6, 2008

Related U.S. Application Data

(63) Continuation of application No. 10/066,515, filed on Jan. 31, 2002, now Pat. No. 7,574,744.

(60) Provisional application No. 60/265,560, filed on Jan. 31, 2001.

(51) Int. Cl.
*A61M 37/00* (2006.01)
*A61M 5/32* (2006.01)
*A61M 25/00* (2006.01)

(52) U.S. Cl. ................ 604/6.03; 604/180; 604/524

(58) Field of Classification Search ........ 604/4.01–6.16, 604/403–413, 257, 258, 96.01, 115, 128, 604/174; 220/62.11–62.22; 435/173.1, 173.3, 435/235.1, 235; 210/257.1, 188, 252, 254
See application file for complete search history.

(56) References Cited

U.S. PATENT DOCUMENTS

| | | | | |
|---|---|---|---|---|
| 1,787,106 A * | 12/1930 | Glazener | ........................ | 248/51 |
| 3,942,528 A * | 3/1976 | Loeser | ........................ | 604/174 |
| 4,340,052 A * | 7/1982 | Dennehey et al. | ............ | 604/317 |
| 6,001,081 A * | 12/1999 | Collen | ........................ | 604/174 |
| 6,113,039 A * | 9/2000 | Riffle | ........................ | 248/75 |
| 6,171,493 B1 * | 1/2001 | Zia et al. | .................... | 210/257.1 |
| 7,686,797 B2 * | 3/2010 | Zia et al. | ........................ | 604/406 |

* cited by examiner

*Primary Examiner* — Leslie Deak
*Assistant Examiner* — Philip R Wiest
(74) *Attorney, Agent, or Firm* — Marshall & Melhorn LLC

(57) ABSTRACT

An improved tubing device, preferably for use in the medical industry is provided. The tubing device provides a seamless transport path by using the tubing itself as the transport means without any other internally wetted parts, or connections, to provide a substantial reduction in the number of fluid contact components, and eliminate the need for cutting tubes into segments to be later bonded via tubing connectors. This can reduce the risk of contamination of the transported materials and can also reduce the use of chemicals such as adhesives and bonding agents.

14 Claims, 7 Drawing Sheets

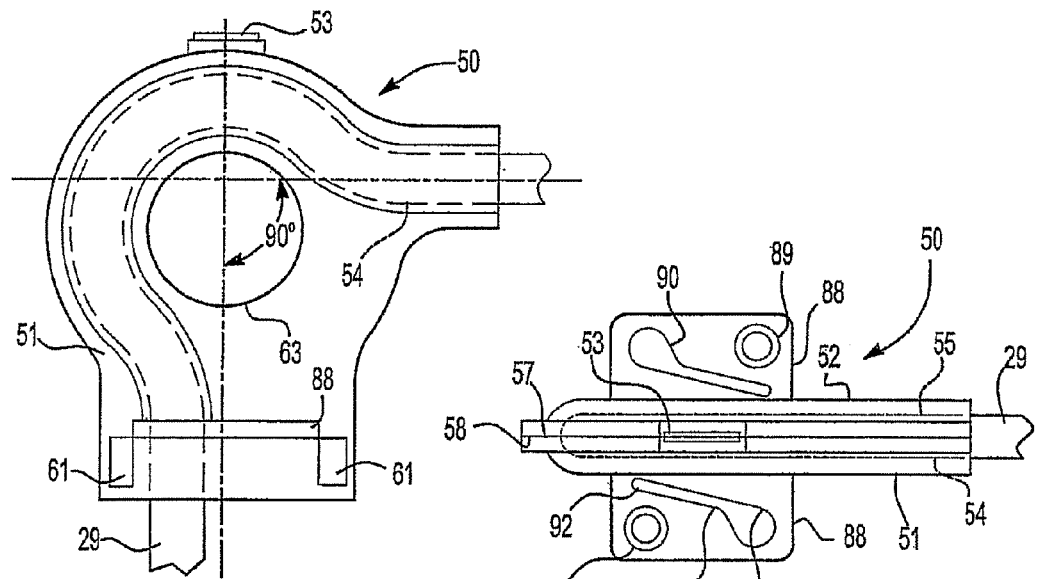
Fig-14
Fig-15
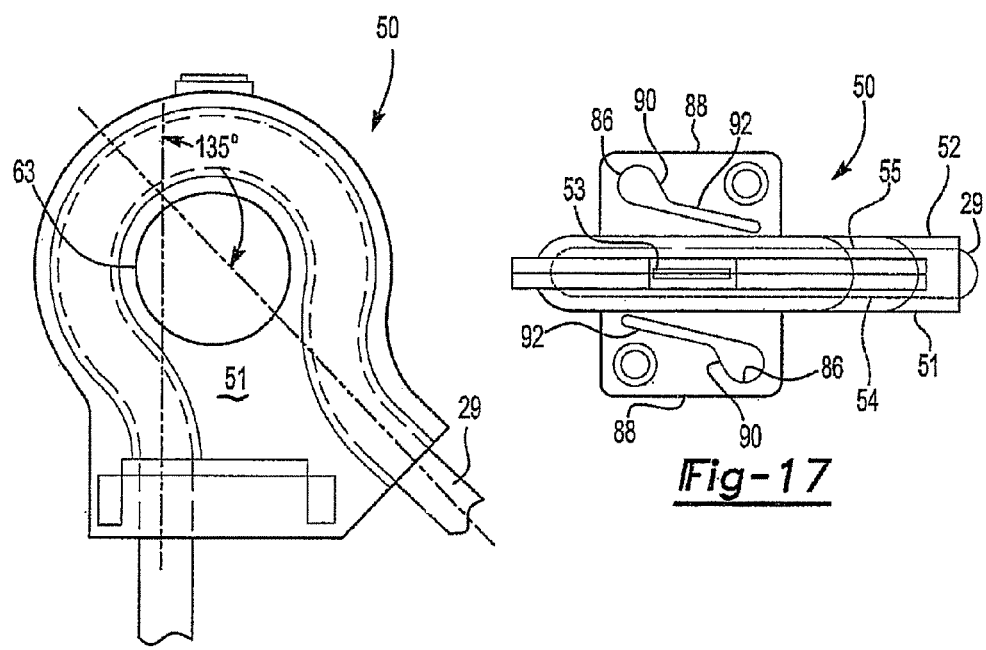
Fig-16
Fig-17

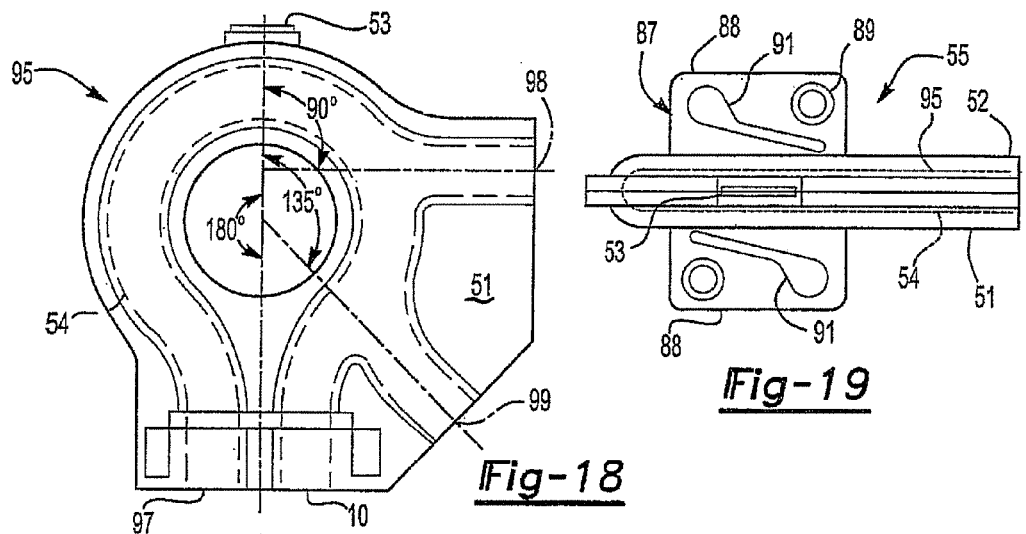
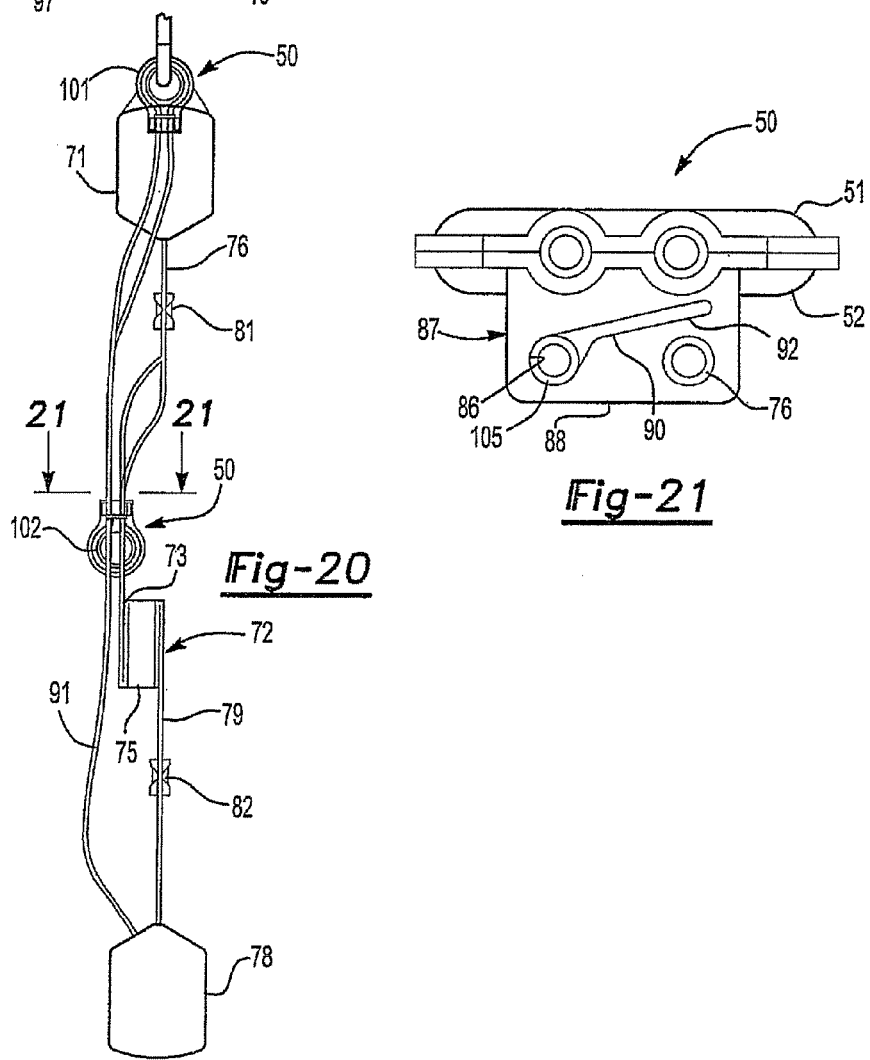

MULTI-PURPOSE TUBING APPARATUS

CROSS REFERENCE TO RELATED APPLICATIONS

This application is a continuation of Utility patent application Ser. No. 10/066,515, filed Jan. 31, 2002, now U.S. Pat. No. 7,571,744 for Multi-Purpose tubing Apparatus. This application claims priority from U.S. provisional patent application Ser. No. 60/265,560, filed on Jan. 31, 2001, and Utility patent application Ser. No. 10/066,515, filed on Jan. 31, 2002. Application Ser. No. 10/066,515 is pending as of the filing date of the present application.

BACKGROUND OF THE INVENTION

1. Field of the Invention

The present invention relates to a device for use with flexible tubing such as that used in various fields which include, but are not limited to, mass transfer, heat transfer, and radiation transfer. More particularly, the present invention relates to a device for holding and/or redirecting such flexible tubing while at the same time providing a convenient way to hold and/or clamp said tubing in a manner which prevents or minimizes kinking of the flexible tubing should weight be applied thereto, such as would occur if the tubing were used to support devices attached thereto. Most particularly, the present invention relates to a device of the foregoing nature that is particularly well suited for flexible tubing sets particularly but not limited to, intravenous fluid administration sets used in the medical field.

2. Discussion of the Related Art

Biological fluid processing methods and apparatus are well known in the art. These apparatus include such as a blood containing bag, a filter, and a blood receiving bag, all connected by flexible tubing. Often it is necessary to change the direction, or reverse the direction, of flow of the flexible tubing used in such apparatus. A known way of doing this is to use a traditional, rigid, U-shaped tubing connector. Such a connector may be formed from a rigid tube by bending it into a "U" shape, and attaching the flexible tubing of the administration set to the connector. However, this presents the problem of how to obtain a leak proof connection between the flexible tubing and the "U" shaped connector. Often, adhesives or other bonding agents are needed, and then the question of maintaining the integrity of the biological fluid being transported becomes critical. This is even more complicated if a piece of tubing is bent into a "U", and additional short tubing pieces are inserted and adhered to the "U" shape to provide for the standard diameter flexible tubing to be press fit onto the "U". Additionally, the smooth fluid flow through the flexible tubing is interrupted by these inserted pieces. This may permit the "U" shaped connector to catch or damage particles and form bubbles in the fluid being transported.

Another known "U" connector is formed by injection molding a material into a desired shape. A one piece connector may be formed by such traditional molding technique, but the process yields a fluid conduit that typically looks more like a "V" than a "U", requires a complicated injection molding technique, and a results in unnecessary higher costs for the device.

Whichever known connector is used, there still remains a significant problem where a reversal in direction (change in direction) in the transfer path is desired without the risks of transport path blockage which may be caused by particle or bubble entrapment due to the significant internal geometrical variations.

Another significant problem in the art is the problem of collapsed tubing, which also may cause transport path blockage, which can negatively impact the fluid flow characteristics. Although there are currently a number of ribbed tubing designs to address the tubing collapse issue, it is desirable to use conventional tubing that is well established particularly in medical applications. Also, the use of standard tubing yields a broader selection of components to be used with the device. For example, commonly used slide, pinch, and roller clamps are not fully functional with the ribbed tubing.

The occurrence of a kink or kinks in flexible tubing under weight bearing situations is also a known problem in the prior art. Such problems can occur, for example, where a "loop" is formed in the tubing, and the loop is hung on a bag hook to support the tubing itself, and/or other articles. A kink in the flexible tubing usually results in the stoppage or impedance of flow or fluid communication, thus disabling or reducing the effectiveness of the system in which it is used. Thus, those skilled in the art continued to search for an improved apparatus to change the direction of flow in flexible tubing without the aforementioned problems.

SUMMARY OF THE INVENTION

The present invention provides a seamless transport path by using the tubing itself as the transport means without any other internally wetted parts, or connections, to provide a substantial reduction in the number of fluid contact components, and eliminate the need for cutting tubes into segments to be later bonded via tubing connectors, all while providing a support member for the tubing which allows the tubing to resist kinking in a weight bearing situation, and to provide for adjustability of the tubing in the support member in certain situations.

In addition to the reduction in the risk of contamination the present invention can reduce the use of chemicals such as adhesives and bonding agents.

In one embodiment of the present invention, at least one curvilinear channel is provided in a support member.

In another embodiment of the present invention, at least one straight channel is provided in a support member.

In a further embodiment of the present invention, a curvilinear channel of less than semi-circular cross section is provided in a support member, and the flexible tubing is attached to the support member in the curvilinear channel. In another embodiment of the present invention, a curvilinear channel of a cross section slightly larger than a semi-circle is provided in the support member, and the flexible tubing is "snapped" into place in the support member.

In a still further embodiment of the present invention, flexible tubing is held in place in annular channels provided in a two-piece support member with the support members being bonded or held to each other.

In a still further embodiment of the invention, an annular channel is molded in a support member and supported by spokes.

In a further embodiment of the invention, a pair of opposed mirror image support members is connected by a hinge, with each support member having a like annular or curvilinear channel formed therein to cover and enclose the flexible tubing when said pieces of said support device are closed and snapped into their retained condition. Alternatively, a similar embodiment can be made wherein the support member, which encases the tube, is formed as a single unit, and the tube is either formed inside the support unit or is later threaded through the support.

It should be understood that the present invention is well suited for gravity driven flows. In particular the device is specifically well suited for gravity driven biological fluid filter applications. A central opening or other device may be provided in the support members to provide for a loop portion in the flexible tubing, and at the same time enable that loop portion to be weight bearing and hung on a traditional IV bag hook.

Thus, it is one possible object of the present invention to provide an improved device for redirecting flexible tubing.

A further object of the present invention can be to provide an externally communicating device which substantially surrounds a flexible tube and holds it in a desired configuration by providing peripheral support on the outer surface of the tubing.

A further object of the present invention can be to provide a substantially "U" shaped turn in a flexible tubing, without sharp corners, to prevent fluid blockages and minimize cell damage.

It can be a further object of the present invention to provide an improved flexible tubing device which has a seamless transport path provided by using the tubing itself as the transport means without any other internally wetted parts or connections.

It can be a further object of the present invention to reduce the risk of contamination while redirecting the flexible tubing by reducing the use of chemicals and bonding agents such as adhesives and solvents.

Another object of the present invention can be to provide an externally communicating device which substantially surrounds a flexible tubing and holds it in a predetermined desired configuration which eliminates bonding sites of previous tubing devices.

Another object of the present invention can be to provide an improved tubing device of the foregoing nature which lends itself to an adjustable design wherein the placement of the tubing device on the flexible tubing may easily be changed at any time.

Another object of the present invention can be to provide a reusable flexible tubing device which may be made of a broad range of materials at a reduced cost.

Further objects and advantages of the present invention will be apparent from the following description and appended claims reference being made to the accompanying drawings forming a part of the specification wherein like reference characters designate corresponding parts in the several views.

BRIEF DESCRIPTION OF THE DRAWINGS

FIG. 14 is a view similar in part to the construction shown in FIG. 12 but wherein the curvilinear channel produces a 90° change in direction instead of a 180° change in direction of the flexible tubing.

FIG. 15 is a top plan view of the construction shown in FIG. 14.

FIG. 16 is an elevational view showing a further modification of the construction illustrated in FIG. 12.

FIG. 17 is a top plan view of the construction shown in FIG. 16

FIG. 18 shows a further modification of the construction shown in FIG. 12 which provides for multiple tubing paths.

FIG. 19 is a top plan view of the construction shown in FIG. 18.

FIG. 20 is a view, similar in part to FIG. 11, but showing two constructions embodying the present invention in use.

FIG. 21 is a top plan view, taken in the direction of the arrows, along the view line 21-21 of FIG. 20.

The above, as well as other advantages of the present invention, will become readily apparent to those skilled in the art from the following detailed description of the preferred embodiments, wherein like numerals designate corresponding parts in the several views.

DESCRIPTION OF THE PREFERRED EMBODIMENTS

Figure 1:
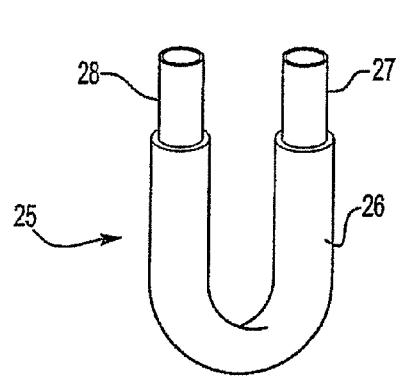
FIG. 1 is a perspective view of a prior art U shaped tubing device.

Referring to FIG. 1 there is shown a device 25 known in the art to produce a reversal of flow or communication path when interposed in a section of flexible tubing. The prior art device 25 comprises a hollow, rigid or semi-rigid, U-shaped tube 26 into which a first connector 27 and a second connector 28 have been sealingly attached by means well known in the art. If flexible tubing, such as IV tubing, is cut, and one end is placed over first connector 27, and the second end is placed over second connector 28, a reversal, or 180° change in the direction of flow occurs.

However, such devices have some or all of the problems of the prior art discussed above. First of all, they are hard to form without introducing narrowing of the passageway and attendant problems. As aforementioned, if it is tried to injection mold these devices, an increase in cost is attendant, and a difficult process is needed. Additionally, such devices are used in biological fluid processing and since fluid touches the rigid tube 26, and the connectors (27, 28), the choice of materials with which to make these prior art devices are limited, as the adhesive and materials must be biocompatible. In addition, once the biological fluid such as blood or blood products touches the device it may not be reusable, thus increasing the cost per use of such devices. Further, failure of such prior art devices will produce non-sterile conditions, resulting in the need to dispose of the biological fluid flowing through the device. Additionally, similar types of issues may be encountered in other applications such as ground water or semiconductor applications where prevention of fluid contamination is of concern.

In order to solve the problems of the known devices, it was desired to produce a device which was, in preferred embodiments, reusable, less prone to failure, adjustable, which had minimal components, which did not touch the fluid being processed, and a device which could be weight bearing.

Figure 2:
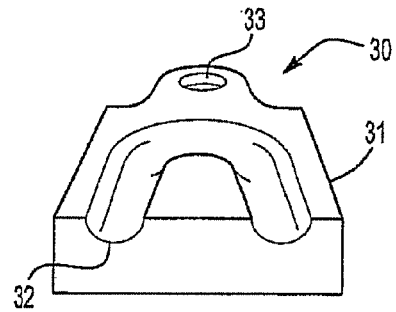
FIG. 2 is a perspective view of a construction embodying the present invention, and having a 180° curvilinear channel formed therein having a cross-section of a semi-circle of a diameter substantially equal to that of the flexible tube it is desired to mount therein.

In order to solve problems of the prior art devices, the improved tubing device 30 shown in FIG. 2 was conceived. The tubing device comprises a support member 31 having a channel 32 formed therein. The curvilinear channel may be such as to reverse the direction of flow or pathway, i.e., U-shaped, produce a 90° in the change of direction of flow, i.e., "right angle" (or be gradually angled in such a manner to result in a final angle in the flow path of about 90 degrees), or of any desired shape to perform any desired change in direction, including having linear portions, if desired. The curvilinear channel may be in a single plane or in multiple planes. An opening or aperture 33 may be provided for hanging the support member 31 from a bag hook 34 (FIG. 11) or other such holding device.

Figure 3:
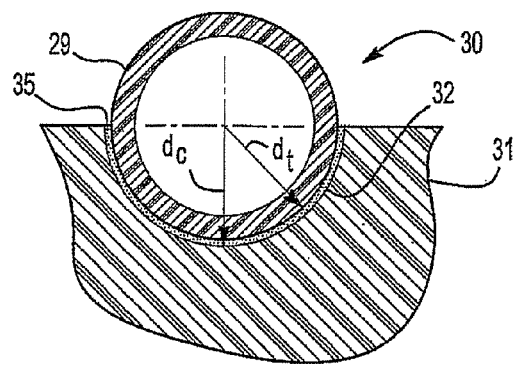
FIG. 3 is a fragmentary sectional, view of a portion of the construction shown in FIG. 2, with a piece of flexible tubing secured in the annular channel.

Referring to FIG. 3, the channel 32 is of a cross-section equal to or less than a semi-circle of a diameter ($d_c$) substantially equal to the diameter ($d_t$) of the flexible tubing that is to be redirected. When the channel 32 is of this cross-section, the tubing preferably is secured by means well known in the art, such as by adhesive 35 to the channel 32. Since the adhesive or other bonding agent being used contacts only the outside of the flexible tubing 29, and the surface of the channel 32, the interior of the tubing is left untouched, thus avoiding problems (e.g. contamination) of the prior art involving adhesive on the flow contacting surfaces of the tubing. Further, the adhesive prevents the tubing 32 from deforming in a weight bearing situation.

Figure 4:
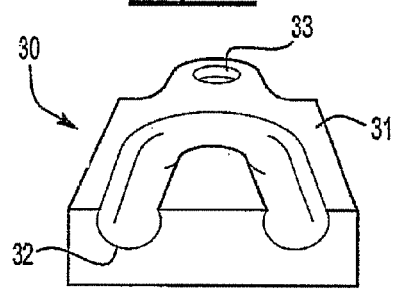
FIG. 4 is a view in large part similar to that of FIG. 2, but showing the channel having a cross-section of slightly larger than a semi-circle, and a diameter substantially equal to that of the flexible tube it is desired to mount therein.
Figure 5:
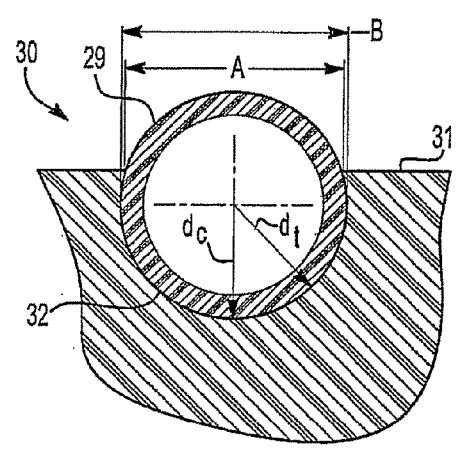
FIG. 5 is a fragmentary sectional view of a portion of the construction shown in FIG. 4, with a piece of flexible tubing secured in the curvilinear channel.

With reference to FIG. 4, an improved tubing device 30 of a construction largely identical to that shown in FIG. 2 is illustrated. The only substantial difference is that the channel 32 provided in a surface of the support member 31 is of a cross-section of slightly larger than a semi-circle of a diameter substantially equal to the flexible tube to be redirected. As shown in FIG. 5, since the opening of the channel 32 is of a dimension A, smaller than the diameter B of the flexible tubing 29, the flexible tubing 29 must first be deformed into an oval shape, and then inserted or "snapped" into the channel 32 where it is retained because of the shape of the channel 32. Regardless of whether the modification of FIG. 2 or FIG. 4 were used to encase the flexible tubing 29, one may place two tubing devices 30 in a 180° opposed, or "channels facing" relationship, and affix them in such relationship. In such configuration, or otherwise, the channels 32 may be of the same or different size or cross-section.

In some applications, such as weight bearing applications, it may be desirable to have the orientation of the channel 32 in the support member 31, at least when it is in substantially a U-shape, such that the legs of the "U" face to the right or left, instead of downward. This is because in a weight bearing situation, with a downwardly facing U-shaped configuration, such as shown in FIG. 4, the flexible tubing 29 at the top of the "U" will tend to deform into an oval shape, and thus possibly disengage from, or "snap-out" of the channel 32 unless the configuration of the channel 32 is modified at the top of the "U" to compensate. Additionally, having the "U" facing downward can further negatively affect flow characteristics of the fluid through the bend.

Figure 6:
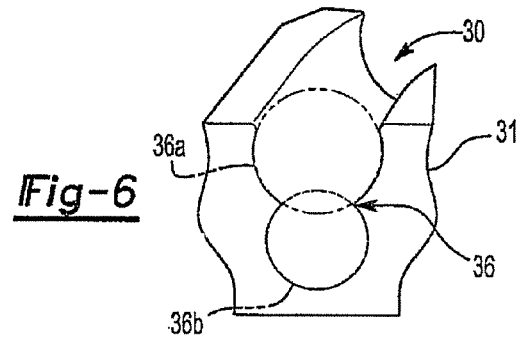
FIG. 6 is a fragmentary elevational view of a modification of the present invention.

FIG. 6 shows a modification of the construction shown in FIG. 5. A two-stage channel 36 is shown in tubing device 30 having a first stage channel 36A, which may be largely identical to the channel 32 shown in FIG. 5, and a second stage channel 36B, which is preferably smaller than the first stage 36A of the two-stage channel 36. The second stage channel 36B would preferably be formed below the first stage channel 36A, but would operate similarly, i.e., the cross-section of second stage channel 36B would be less than, equal to, or slightly larger than a semi-circle of the diameter of the tubing which is desired to be inserted into second stage channel 36B.

Figure 6A:
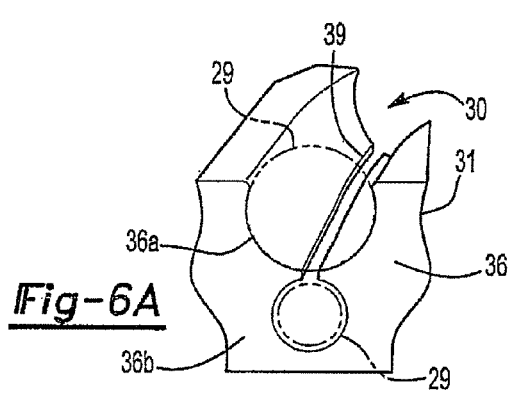
FIG. 6A is a modification of the construction shown in FIG. 6.

If it is desired to use two flexible tubes 29 simultaneously, the modification shown in FIG. 6A may be used wherein the first stage channel 36A may be separated completely from the second stage channel 36B by a slot 39 in support member 31. The width "W" of slot 39 is preferably substantially equal to twice the thickness of the flexible tubing 28 which is to be inserted into slot 39. This allows the flexible tubing to be suitably deformed (squeezed together or compressed) to bring the walls of the flexible tubing 29 together before insertion into slot 39. After the tubing 29 is deformed and inserted through the slot 39 and into second channel 36B, it will expand into its proper shape and be held in place.

Figure 7:
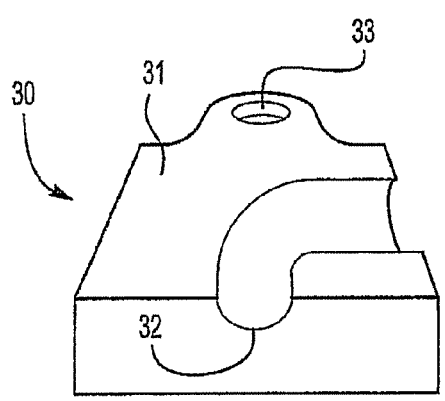
FIG. 7 is a perspective view of a modification of the present invention having a 90° curvilinear channel formed in a top surface thereof.
Figure 8:
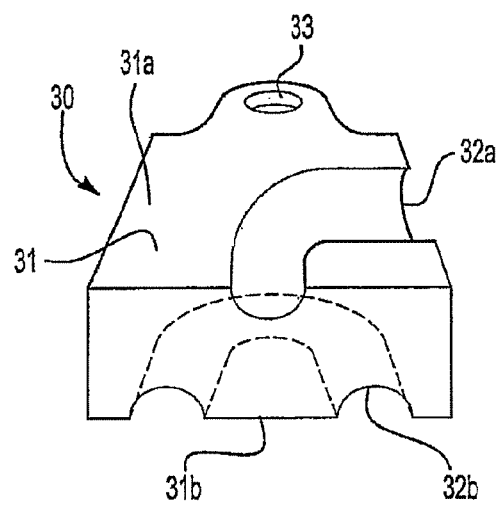
FIG. 8 is a perspective view of a further modification of the present invention, similar in part to FIG. 7, but showing a 180°, or "U" shaped channel on one side of the support member, and a 90°, or right angle, channel formed in the lower side of said support member.

Referring now to FIGS. 7 and 8 a further modification of the present invention is shown. In the improved tubing device 30 illustrated in FIG. 7, the channel 32 makes a 90° bend, instead of the 180° turn illustrated in FIG. 2. In the improved tubing device 30 illustrated in FIG. 8, there is a top channel 32A which makes a 90° bend formed in the top surface 31A of the support member 31, and bottom channel 32B, making a 180° bend, formed in the bottom surface 31B of support member 31.

Channel(s) 32 may be formed in one or more surfaces of a support member 31, and the shape of the channel(s) 32 formed in one of the surfaces of the support member 31 may, or may not be, of the same shape or curvature of channel(s) 32 formed in any of the other surfaces of the support member 31. Channel(s) 32 may contain linear or other shaped portions as well.

Figure 9:
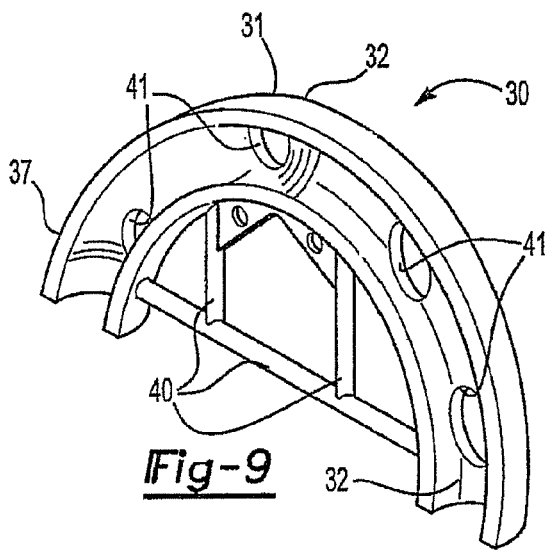
FIG. 9 is a perspective view showing a further modification of the present invention.

With reference to FIG. 9, there is shown a further modification of the improved tubing device 30 of the present invention which is especially useful in medical devices. In the illustrated embodiment, the channel(s) 32 is semi-circular in shape, and the support member 31 is substantially a semi-circular trough 37 containing channel 32, with suitable spokes or supports 40 helping to keep the shape of the trough 32. Holes or apertures 41 may be provided in the support member 31 to save weight, if desired, and to increase visibility of the flexible tubing 29. The cross-section of the channel 32 may be more or less than a semi-circle of a diameter of the tubing it is desired to support, as previous described. Because of the open construction of the improved tubing device 31 it may easily be hung on a bag hook 34 (FIG. 11) and, therefore, the loop in the flexible tubing 29, after placement in the curvilinear channel 32, now becomes weight bearing.

Since the application of weight to the flexible tubing will tend to deform it, if more than a minimal amount of weight is to be carried, the cross-section of the trough may be of a cross-section of somewhat greater than a semi-circle, for example, two-thirds of a circle. Thus the opening through which the tube is inserted is less than the diameter of the flexible tube. Or, there may be a lip on the lower edge of the trough.

If it is desired to encase the flexible tubing 29, two of the improved tubing devices 30 having trough 37 may be placed in an 180° opposed relationship.

Figure 9A:
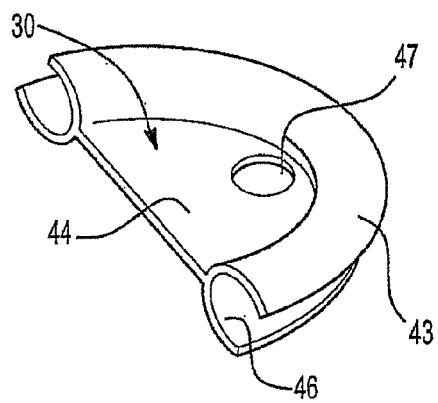
FIG. 9A is a modification of the construction shown in FIG. 9.
Figure 11:
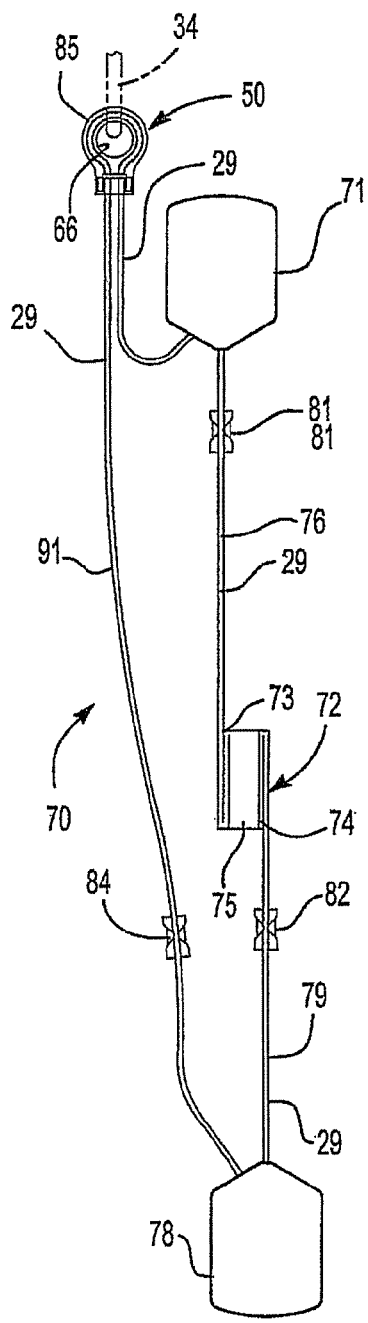
FIG. 11 is a diagrammatic view showing one possible use of the construction shown in FIG. 10.

FIG. 9A shows a modification of the construction shown in FIG. 9 which is particularly useful in the weight bearing situations discussed above. Since the flexible tubing 29 will tend to flatten out when weight is applied thereto, it is desirable to have a construction that will resist this flattening, as well as prevent the disengagement discussed above. This is accomplished by the improved tubing device 30 shown in FIG. 9A. There is shown an upwardly facing trough 43 supported by a web 44. The cross-section of the trough is that of an annular shape of about two-thirds of a circle. Therefore, outwardly facing channel 46 has a cross-section of about two-thirds of a circle. When the flexible tube 29 has weight applied, it will try to flatten in a horizontal or lateral direction, and the sidewalls of the tube will try to move sideways. However, they are blocked from doing this by the sidewalls of the radially outwardly facing channel 46, thus the flexible tube 29 cannot collapse on itself and shut off the flow of fluid being filtered. A hole or aperture 47 is provided in the web 44 for hanging the improved tubing device 31 on a bag hook 34 (FIG. 11).

Figure 10:
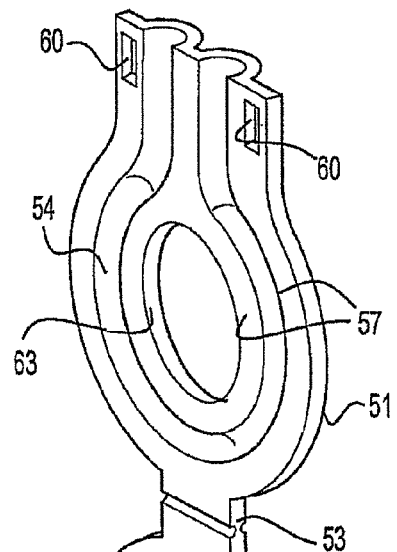
FIG. 10 is a perspective view showing a further modification of the present invention.

The modifications of the improved tubing device of the present invention, which have been shown thus far, have not completely encased the flexible tubing whose direction is being affected. A further modification of the present invention that does completely encase the flexible tubing is shown in FIG. 10. This embodiment uses the same principles heretofore described, and has been found to be particularly useful in biological fluid filtration systems, such as that shown in FIG. 11. For ease of understanding, the modifications of the invention to be described hereinafter will be referred to as a two part improved tubing device and indicated by the numeral 50 although, as will become clear, they can be formed in a single piece with a hinge connecting a first portion and a second portion. Although shown with rough or sharp edges for purposes of illustration, it is preferred that smooth and/or rounded edges be incorporated in the tubing devices of the present invention to prevent punctured bags/tubes and packaging.

Referring specifically to FIG. 10, the improved two-part tubing device 50 has a first portion 51 and a second portion 52 connected by a hinge 53, which may be any type of hinge construction well known in the art. First portion 51 of two-part tubing device 50 has a first channel portion or passageway 54 formed therein, while second portion 52 of two-part tubing device 50 has a second channel or passageway 55 formed therein. The first portion 54 and the second portion 55 are placed such that when the first portion 51 of two part tubing device 50 is closed, i.e., brought into an opposed facing relationship with second portion 52, the first portion of passageway 54 will be directly opposite the second portion of passageway 55, and the two together will form a circular or substantially circular channel or passageway 56 (FIG. 13) to capture a flexible tubing 29 whose direction is to be rerouted. The dimensions for the first passageway portion 54, and second passageway portion 55 and, thus, the diameter of the circular passageway, may be chosen depending on the application. The circular passageway may be slightly smaller than the flexible tubing that is being rerouted such that the tubing is held in slight compression and will not be prone to slippage in the circular passageway 56 formed by first portion 54 and second portion 55. The provision of a sharp 'S' bend in the passageway will also help prevent slippage. The flexible tubing will not slip if pulled on one end because of the S shape of the passageway.

The shape of the passage way 54 and passage way 55 may not necessarily be the same but complimentary, as it may be preferable to snap the tubing in one side such as first passageway 54 of first portion 51 prior to mating of the two portions 51 and 52.

When closed, first mating surface 57 provided on first portion 51 of two-part tubing device 50 will be in contact with or closely adjacent second mating surface 58 provided on second portion 52 of two-part tubing device 50.

A pair of apertures, openings, or eyes 60 provided in first mating surface 57 will receive a pair of hooks or protrusions 61 provided on second lower surface 58, which will fixedly, but removably, keep first portion 51 and second portion 52 together to keep two-part tubing device 50 in its closed position. The protrusions 61 may be recessed to prevent sharp edges. In operation the operator would place the flexible tubing into the first portion of channel 54 formed in first portion 51 of two part tubing device, and then close the second portion 52, or vice versa. When first portion 51 and second portion 52 are brought together and closed, a first central opening 63 provided in first portion 51 will become in mating or opposed contact with second central opening 64, providing a central opening 66 which may be used to hang the tubing device on a bag hook 34 (FIG. 11), or the like.

Two-part tubing device 50 has proved particularly useful in biological fluid filtration or dispensing systems. It especially is useful in such biological fluid filtration or gravitational dispensing systems where a loop or elevated portion is used for automating and increasing recovery from a gravitational dispensing of fluid.

FIG. 11 illustrates such a system which is disclosed in U.S. Letters Pat. No. 6,171,493. Biological fluid filtration system 70 has a blood container or bag 71 provided upstream from, and elevated above, a leukocyte depletion device 72. The leukocyte depletion device 72 has an inlet 73 and an outlet 74 separated by a filter media 75. Blood container 71 is connected to, or in fluid communication with said leukocyte depletion device 72 through first conduit 76.

There is also provided a blood-receiving container 78 downstream of the leukocyte depletion device 72. Leukocyte depletion device 72 is connected to blood receiving container 78 through second conduit 79. An inlet clamp 81 and an outlet clamp 82 may be provided. A bypass line 91 is provided which may be in fluid communication with the blood container 71 and blood receiving container 78. Bypass clamp 84 may be provided in bypass line 91.

In order for the closed loop leukocyte depletion system 70 to work, it is necessary that a "loop" 85 of the bypass line 91 be elevated to a sufficient height to prevent the passage of fluid around the leukocyte depletion device. This proved difficult to do in practice until the two part improved tubing device 50 of the present invention was developed. Tubing device 50 is shown hanging from a bag hook 34. The loop portion 85 of the by pass line 91 is positioned such that when the blood container 71 is full of blood, the blood will not reach the loop portion 85, and thus there can be no flow of blood through the by pass line 91.

The operation of the biological fluid filtration system 70 with the two part tubing device 50 remains identical to that described in applicant's aforementioned co-pending patent application.

Figure 11A:
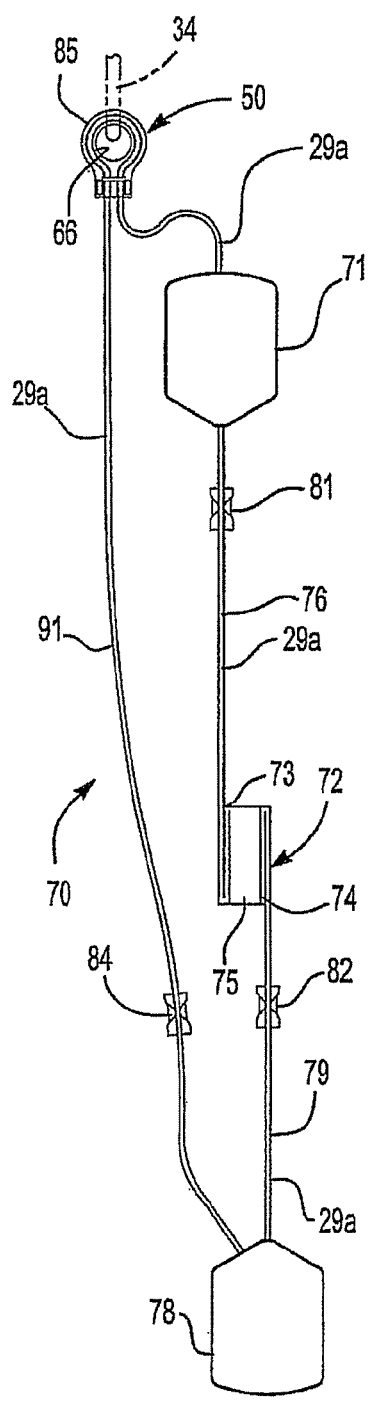
FIG. 11A is a diagrammatic view showing a modification of the system depicted in FIG. 11.

A variation on the device shown in FIG. 11 is depicted in FIG. 11A. This embodiment is very similar to that shown in FIG. 11 except that the flexible tubing 29 is replaced by flexible tubing 29A, which connects to the top of the blood container 71 as opposed to the bottom of the container 71, as was depicted in FIG. 11. This variation can be preferable in certain applications. Other than the relocation of tubing 29A, this embodiment can be substantially identical to that shown in FIG. 11. flexible tube 29A is threaded through the tube-holder 50, which supports the tube and substantially prevents crimping or deformation of the tube 29A.

Figure 12:
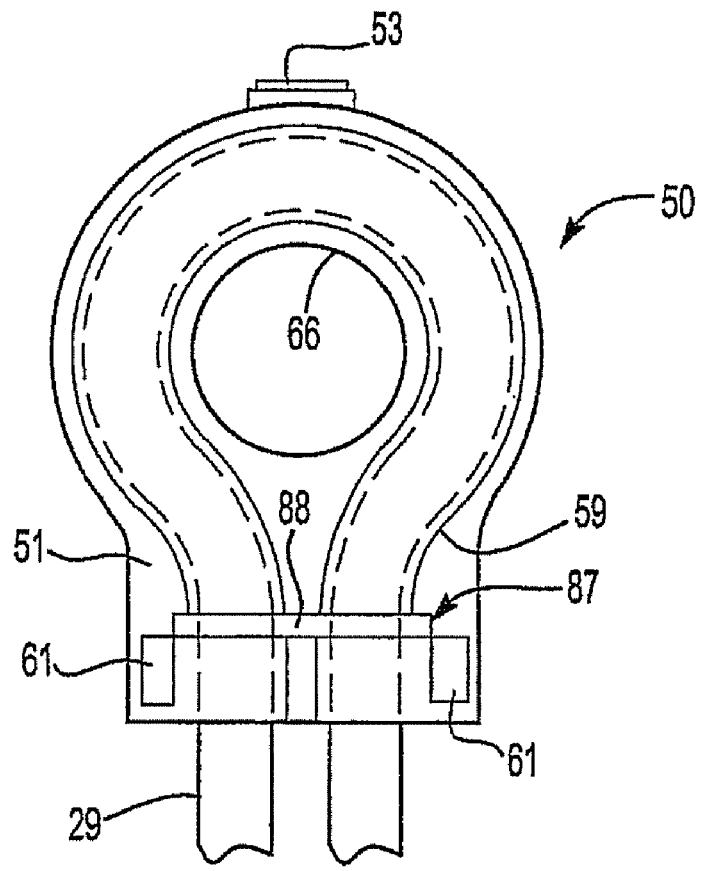
FIG. 12 is an elevational view showing the construction of FIG. 10 in its closed or snapped together position.

Referring to FIG. 12 the construction of FIG. 10 is shown in its closed position. The clamp portion 87 of the two-part tubing device 50 can be clearly seen in FIG. 13. Clamp portion 87 takes the form of an upstanding wall 88 which extends substantially vertically from first portion 51 of the two part tubing device 50. Upstanding wall 87 has a tubing opening 89 of a predetermined desired size such that flexible tubing 29 can pass therethrough, and a clamp opening 90 having a wider portion 86 into which tubing can pass through easily, and a narrowed portion 92 having a width essentially twice that of, or perhaps slightly less, than the wall thickness of the flexible tubing 29, such that when the tubing is moved from the wider portion 86 of the clamp opening 90 into the narrowed portion 92 the walls of the flexible tubing 29 are essentially pushed together and brought into contact, thereby cutting off the fluid flow through the tubing that is in the clamp opening 90.

Figure 13:
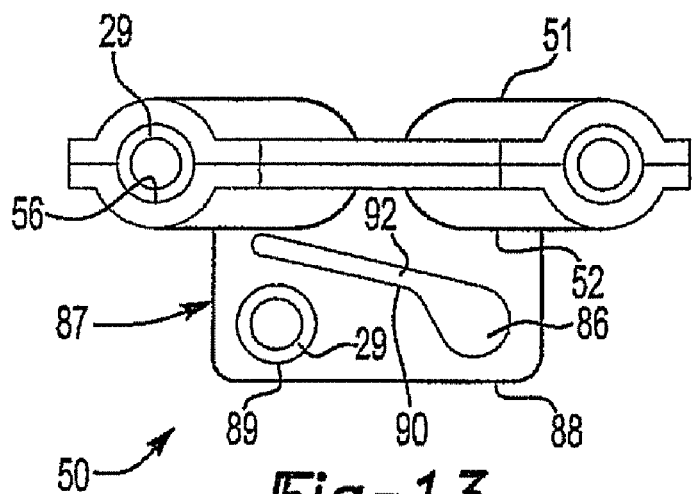
FIG. 13 is a sectional view, taken in the direction of the arrows, along the section line 13-13 of FIG. 12.

The construction shown in FIGS. 14 and 15 is in large part similar to the construction shown in FIGS. 12 and 13. The only substantial difference between the constructions is the fact that the first portion 51 and second portion 52 of the improved two part tubing device 50 have been modified so that the first portion 54, and the second portion 55 of the circular channel 56 are shaped so as to change the flexible tubing by making a 90° bend in the same instead of a 180° bend. In addition, there are multiple clamp portions 87, one extending from each side of the two-piece tubing device 50.

Similarly, the construction shown FIGS. 16 and 17 is substantially identical to that shown in FIGS. 14 and 15, except that the first portion 51 and the second portion 52 of the improved two piece tubing device 50 have been modified to provide for changing the direction of the tubing for 1350 rather than the 90° shown in FIGS. 14 and 15.

Referring to FIGS. 18 and 19, there is shown a further modification of the two-piece tubing device 50 previously illustrated. For clarity of understanding, this device is referred to as a multi-path two-piece tubing device, and indicated by the numeral 95. In this construction the first portion 51 and the second portion 52 of the multi-path two-piece tubing device 95 still have the first portion 54 and the second portion 55 of the curvilinear channel or passageway formed therein. However, the circular passageway 51 formed by the combination of the first portion 54 and the second portion 55 no longer has a single inlet and a single outlet, but rather one possible inlet point indicated by the numeral 97, and multiple outlet points, such as first branch 98, second branch 99, and third branch 100 to provide for a change in direction of the flexible tubing by 90°, 135°, and 180° respectively. The remainder of the construction stays substantially the same.

Referring now to FIGS. 20 and 21, the use of our improved two part tubing device is shown in a biological fluid filtration system similar in part to that illustrated in FIG. 11 but requiring a first tubing loop 101 and a second tubing loop 102, both formed using the improved two part tubing device 50 of the present invention. Clearly the multi-path two portion tubing device 95 just described could also be used. In this modification, not only is flexible tubing 29 held in the passageway created within the first portion 51 and second portion 52 of the two part tubing device 50, but the first conduit 76 providing fluid communication between the blood bag 71 and the leukocyte filtration device 72 passes through the tubing opening 89 and a second flexible tubing 105 passes through the clamp opening 90, and can be clamped and unclamped as desired, resulting in the need for one less tubing clamp for the operation of the system illustrated. The use of multiple tubes traveling in multiple paths is well within the scope of the present invention.

Figure 22:
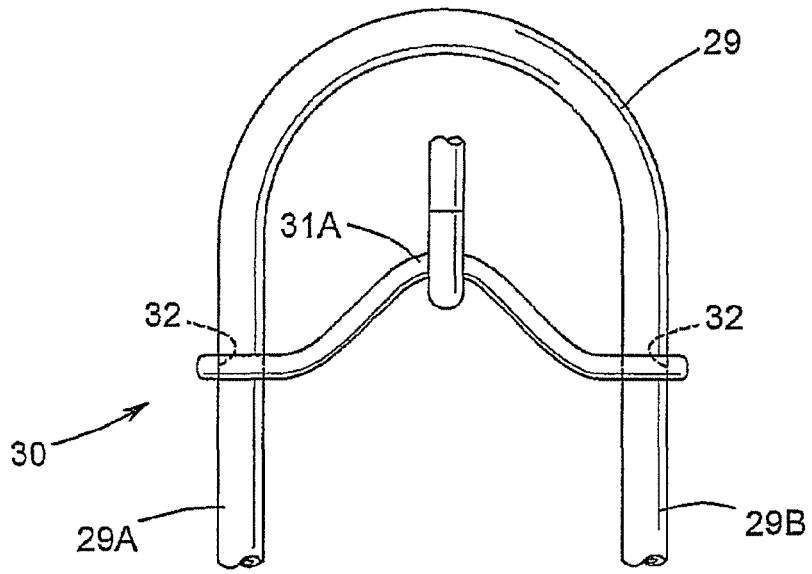
FIG. 22 is an elevational view of a further modification of the present invention.
Figure 23:
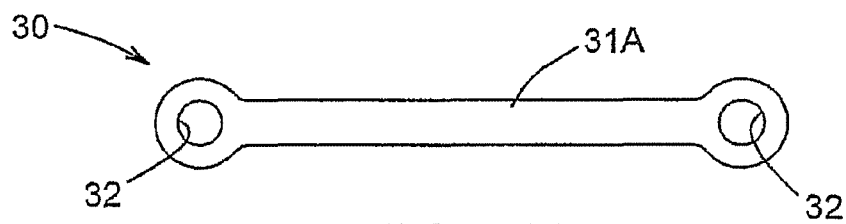
FIG. 23 is a top plan view of the construction shown in FIG. 22.

Referring now to FIGS. 22 and 23, there is shown a further modification of the improved tubing device 30 embodying the present invention, and having a flexible support member 31A having at least one, and preferably a pair of channels 32, formed proximate the ends thereof. Flexible tubing 29 will pass through the channels 32 and form a U shape above the flexible support member 31A. The flexible support member may hang on a hook for support.

Depending on the application, channels 32 may be of a diameter slightly less than, substantially equal to, or slightly larger than, the diameter of the flexible tubing 29. If adjustability is highly desired, it would be preferred to make the channels 32 larger than the tubing 29. If the channels 32 are smaller than the tubing 29, there would be substantially no adjustability. If the channels 32 are substantially the same, the position of the tubing 29 will be adjustable, when desired. A first leg 29A of the tubing 29 leg needs to be pulled, while the second leg 29B of the tubing 29 is pushed to adjust the length of each leg position of the loop.

These same considerations as to the size of the channel 32 in relationship to the size of the tubing 29 will apply to any embodiment of the invention where at least a portion of the tubing 29 is encased, surrounded or encircled by at least one, and preferably two channels 29, such as shown, by way of example and not of limitation, in FIGS. 10-21.

Figure 24:
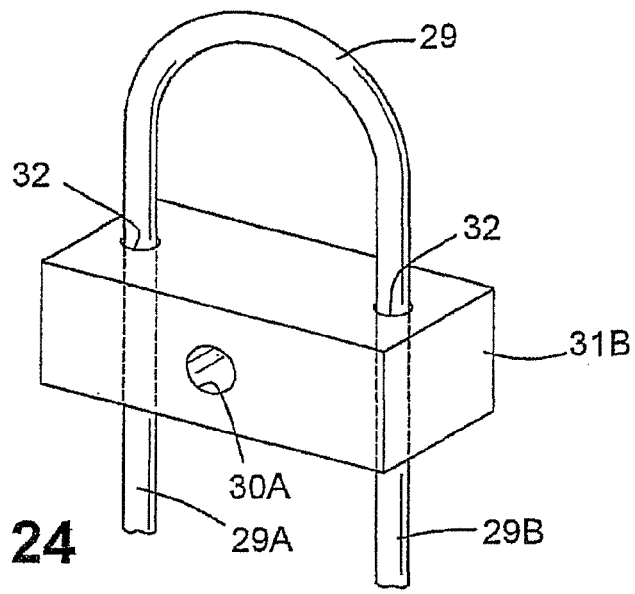
FIG. 24 is a perspective view of a further modification of the present invention.

Referring now to FIG. 24, a modification of the present invention is shown comprising a rigid or semi-rigid support member 31B, having a hole or aperture 30A therein by which the support member 31B may be hung by a hook or other well known support means. A pair of channels 32 are provided in predetermined desired positions in support member 31B, and flexible tubing 29 is passed through channels 32 to form a U shaped (upright or inverted) loop. The size of the channels with respect to the tubing will be chosen as discussed hereinabove, depending on the degree of adjustability desired.

Thus, by carefully considering the problems in the art, a novel tubing device to capture and redirect flexible tubing, while at the same time to enable it to be weight bearing, has been provided.

What is claimed is:

1. A biological fluid filtration system comprising:
   a blood container;
   a leukocyte depletion device, said leukocyte depletion device having an inlet and an outlet with a filter media disposed there between, said leukocyte depletion device being disposed downstream from said blood container;
   a first conduit, said blood container and said inlet of said leukocyte depletion device being in fluid communication through said first conduit;

a blood-receiving container, said blood receiving container being disposed downstream of said leukocyte depletion device;

a second conduit, said outlet of said leukocyte depletion device being in fluid communication with said blood receiving bag through said second conduit;

a bypass line, said bypass line providing fluid communication between said blood container and said blood receiving container;

said bypass line comprising a loop, said loop of said bypass line being configured to be disposed above said blood container at a sufficient height to prevent the passage of fluid around the leukocyte depletion device; and a one piece tube support device, said loop of said bypass line being disposed in said one piece tube support device, said one piece tube support device comprising a curvilinear channel of substantially circular cross-section and of a diameter substantially that of the bypass line for receiving the bypass line;

and completely surrounding the bypass line, thereby being configured to prevent slippage of the bypass line and support substantially the entire weight of said biological fluid filtration system without substantially crimping said bypass line.

2. The biological fluid filtration system according to claim 1, wherein said bypass line connects to the top of said blood container.

3. The biological fluid filtration system according to claim 1, wherein said bypass line connects to the bottom of said blood container.

4. The biological fluid filtration system according to claim 1, wherein said one piece tube support device comprises:
a tube support comprising a U-shaped curvilinear channel disposed therein for receiving a piece of tubing; and
means for holding a piece of tubing in said channel.

5. The biological fluid filtration system according to claim 1, wherein said one piece tube support device comprises:
a tube support comprising a curvilinear channel disposed therein for receiving a piece of tubing; and
structure to hold a piece of flexible tubing in said channel.

6. A biological fluid filtration system comprising:
a blood container having an outlet;
a leukocyte depletion device, said leukocyte depletion device having an inlet and an outlet with a filter media disposed there between;
a blood-receiving container, said blood receiving container having an inlet;
a first conduit, said outlet of said blood container and said inlet of said leukocyte depletion device being in fluid communication through said first conduit;
a second conduit, said outlet of said leukocyte depletion device being in fluid communication with said inlet of said blood receiving bag through said second conduit;
a bypass line, said bypass line providing fluid communication between said blood container and said blood receiving container;
said bypass line comprising a loop, said loop of said bypass line being configured to be disposed above said blood container at a sufficient height to prevent the passage of fluid around the leukocyte depletion device; and
a hinged unitary tube support device, said loop of said bypass line being disposed in said hinged unitary tube support device, and said hinged unitary tube support device comprising a curvilinear channel of substantially circular cross-section disposed therein for receiving the bypass line and completely enclosing the bypass line, the diameter of the substantially circular cross-section being substantially that of the bypass line, the device thereby being configured to support substantially the entire weight of said biological fluid filtration system without substantially crimping said bypass line.

7. A biological fluid filtration system comprising:
a blood container;
a leukocyte depletion device, said leukocyte depletion device having an inlet and an outlet with a filter media disposed there between, said leukocyte depletion device being disposed downstream from said blood container;
a first conduit, said blood container and said inlet of said leukocyte depletion device being in fluid communication through said first conduit;
a blood-receiving container, said blood receiving container being disposed downstream of said leukocyte depletion device;
a second conduit, said outlet of said leukocyte depletion device being in fluid communication with said blood receiving bag through said second conduit;
a bypass line, said bypass line providing fluid communication between said blood container and said blood receiving container;
said bypass line comprising a loop, said loop of said bypass line being configured to be disposed above said blood container at a sufficient height to prevent the passage of fluid around the leukocyte depletion device; and
a tube support device, said loop of said bypass line being disposed entirely inside said tube support device, said tube support device comprising a unitary, hinged, tube support device having a curvilinear channel of substantially circular cross-section and a diameter substantially that of the bypass line disposed therein for receiving the bypass line, thereby being configured to support substantially the entire weight of said biological fluid filtration system without substantially crimping said bypass line.

8. A biological fluid filtration system comprising:
a blood container;
a leukocyte depletion device, said leukocyte depletion device having an inlet and an outlet with a filter media disposed there between, said leukocyte depletion device being disposed downstream from said blood container;
a first conduit, said blood container and said inlet of said leukocyte depletion device being in fluid communication through said first conduit;
a blood-receiving container, said blood receiving container being disposed downstream of said leukocyte depletion device;
a second conduit, said outlet of said leukocyte depletion device being in fluid communication with said blood receiving bag through said second conduit;
a bypass line, said bypass line providing fluid communication between said blood container and said blood receiving container;
said bypass line comprising a loop, said loop of said bypass line being configured to be disposed above said blood container at a sufficient height to prevent the passage of fluid around the leukocyte depletion device; and
a one piece tube support device, said loop of said bypass line being disposed in said one piece tube support device, and said one piece tube support device comprising a curvilinear channel for receiving the bypass line, the curvilinear channel being of a U-shape, wherein the open end of the U is narrower than the closed end, the one piece tube support device thereby being configured to prevent slippage of the bypass line and support substantially the entire weight of said biological fluid filtration system without substantially crimping said bypass line.

9. The biological fluid filtration system according to claim 8, wherein said bypass line connects to the top of said blood container.

10. The biological fluid filtration system according to claim 8, wherein said bypass line connects to the bottom of said blood container.

11. The biological fluid filtration system according to claim 8, wherein said one piece tube support device comprises:
a tube support comprising a U-shaped curvilinear channel disposed therein for receiving a piece of tubing; and
means for holding a piece of tubing in said channel.

12. The biological fluid filtration system according to claim 8, wherein said one piece tube support device comprises:
a tube support comprising a curvilinear channel disposed therein for receiving a piece of tubing; and
structure to hold a piece of flexible tubing in said channel.

13. A Biological fluid filtration system comprising:
a blood container;
a leukocyte depletion device, said leukocyte depletion device having an inlet and an outlet with a filter media disposed there between, said leukocyte depletion device being in fluid communication through said first conduit;
a blood-receiving container, said blood receiving container being disposed downstream of said leukocyte depletion device having an inlet and an outlet with a filter media disposed there between, said leukocyte depletion device being disposed downstream from said blood container
a first conduit, said blood container and said inlet of said leukocyte depletion device being in fluid communication through said first conduit;
a blood-receiving container, said blood receiving container being disposed downstream of said leukocyte depletion device;
a second conduit, said outlet of said leukocyte depletion device being in fluid communication with said blood receiving bag through said second conduit;
a bypass line, said bypass line providing fluid communication between said blood container and said blood receiving container;
said bypass line comprising a loop, said loop of said bypass line being configured to be disposed above said blood container at a sufficient height to prevent the passage of fluid around the leukocyte depletion device; and
a single component tube support device, said loop of said bypass line being disposed in said single component tube support device, said single component tube support device comprising a curvilinear channel disposed therein for receiving the bypass line and completely enclosing the bypass line, the curvilinear channel having a U-shape wherein the open end of the U is narrower than the closed end, the single component tube support device thereby being configured to support substantially the entire weight of said biological fluid filtration system without substantially crimping said bypass line.

14. A biological fluid filtration system comprising:
a blood container;
a leukocyte depletion device, said leukocyte depletion device having an inlet and an outlet with a filter media disposed there between, said leukocyte depletion device being disposed downstream from said blood container;
a first conduit, said blood container and said inlet of said leukocyte depletion device being in fluid communication through said first conduit;
a blood-receiving container, said blood receiving container being disposed downstream of said leukocyte depletion device;
a second conduit, said outlet of said leukocyte depletion device being in fluid communication with said blood receiving bag through said second conduit;
a bypass line, said bypass line providing fluid communication between said blood container and said blood receiving container;
said bypass line comprising a loop, said loop of said bypass line being configured to be disposed above said blood container at a sufficient height to prevent the passage of fluid around the leukocyte depletion device; and
a tube support device, said loop of said bypass line being disposed entirely inside said tube support device, said tube support device comprising a unitary, hinged, tube support device having a curvilinear channel disposed therein for receiving the bypass line, the curvilinear channel having a U-shape wherein the open end of the U is narrower than the closed end, the tube support device thereby being configured to support substantially the entire weight of said biological fluid filtration system without substantially crimping said bypass line.

* * * * *